US005753704A

United States Patent [19]

Lindner et al.

[11] Patent Number: 5,753,704
[45] Date of Patent: May 19, 1998

[54] THERAPEUTIC COMPOSITIONS COMPRISING UNSATURATED DIOIC ACIDS OR DERIVATIVES THEREOF

[75] Inventors: Nigel Lindner, Higham Ferrers; John Casey, Stanwick, both of United Kingdom

[73] Assignee: Unichema Chemie B.V., Gouda, Netherlands

[21] Appl. No.: 411,750

[22] PCT Filed: Aug. 27, 1993

[86] PCT No.: PCT/GB93/02006

§ 371 Date: May 19, 1995

§ 102(e) Date: May 19, 1995

[87] PCT Pub. No.: WO94/07837

PCT Pub. Date: Apr. 14, 1994

[30] Foreign Application Priority Data

Sep. 30, 1992 [GB] United Kingdom ............... 9220667

[51] Int. Cl.$^6$ .................. C07C 57/13; A61K 7/48
[52] U.S. Cl. .................. 514/560; 514/558; 514/547; 514/613; 514/616; 514/706; 514/738; 514/859
[58] Field of Search .................. 514/558, 560

[56] References Cited

U.S. PATENT DOCUMENTS 2,957,907 10/1960 Payne et al. .
3,497,435 2/1970 Wimer et al. .
3,793,367 2/1974 Diekman .

FOREIGN PATENT DOCUMENTS 296506 12/1988 European Pat. Off. .
2244485 4/1975 France .
698091 10/1940 Germany .
482666 12/1969 Switzerland .

OTHER PUBLICATIONS

Otieno, et al: "Thermal Acid–Catalysed Rearrangements of Natural Chrysanthemic Acid", Journal of the Chemical Society, Perkin Transactions I, No. 2, 1977, pp. 196–201.

Primary Examiner—Rebecca Cook
Attorney, Agent, or Firm—Pillsbury Madison & Sutro LLP

[57] ABSTRACT

Disclosed are certain novel polyunsaturated dioic acids having between 8 and 16 carbon atoms (inclusive), excluding those compounds in the group consisting of: 2,5 octadienedioic acid; 1,7 octadienedioic acid; 2,4,6 octatrienedioic acid; and 1,3,5,7 nonatetraenedioic acid; 2,5,8 decatrienedioic acid; 3,6 dodecadienedioic acid; 3,13 hexadecadienedioic acid. Also disclosed are pharmaceutical or cosmetic compositions comprising unsaturated dioic acids and certain of their derivatives. Also disclosed are methods of treating human skin and a method of preparing unsaturated dioic acids.

7 Claims, 4 Drawing Sheets ns is a 371 of PCT/GB93/02006 filed Aug. 27, 1993 published as WO94/07837 Apr. 14, 1994.

THERAPEUTIC COMPOSITIONS COMPRISING UNSATURATED DIOIC ACIDS OR DERIVATIVES THEREOF

This is a 371 of PCT/GB93/02006 filed Aug. 27, 1993 published as WO94/07837 Apr. 14, 1994.

FIELD OF THE INVENTION

This invention relates to unsaturated dioic acids, that is, unsaturated aliphatic dicarboxylic acids, especially $C_8$–$C_{22}$ compounds, particularly, but not exclusively, $C_{16}$ and $C_{18}$ unsaturated dioic acids (i.e. those having 16 or 18 carbon atoms), and concerns certain novel $C_8$–$C_{16}$ dioic acids, a method of producing dioic acids, and their use in the treatment of skin for medical and cosmetic purposes, such as acne treatment and skin lightening.

BACKGROUND OF THE INVENTION

It is known to use saturated dioic acids (having the general formula COOH $(CH_2)_n$COOH) for the treatment of skin for medical and cosmetic purposes. For example, U.S. Pat. No. 4,386,104 (Nazzaro-Porro) discloses saturated dioic acids, containing 7 to 13 carbon atoms, for the treatment of acne and other skin conditions.

In particular, the $C_9$ saturated dioic acid ("azelaic" acid) having the formula COOH$(CH_2)_7$COOH, is frequently cited as being effective in the treatment of acne and other skin conditions, and in the lightening of skin.

Thus far, unsaturated dioic acids have not been readily commercially available, although a method of synthesising certain unsaturated dioic acids is disclosed in EP 0229252. Indeed some of this class of molecules have not previously been described. However, it is known that certain unsaturated dioic acids, particularly certain $C_6$, $C_8$, $C_{10}$ and $C_{12}$ mono-unsaturated dioic acids can be detected in the urine of patients with medium chain acyl-CoA dehydrogenase deficiency (Jin & Tserng [1989] Journal of Lipid Research 30, 1612–1619 and Tserng et al., [1990] Journal of Lipid Research 31, 763–771). Certain other unsaturated dioic acids are disclosed in various other publications.

EP 0341796 discloses a microbial route using *Candida cloacae* beta-oxidation mutants for the production of saturated dioic acids from longer chain saturated fatty acids (monocarboxylic acids) or triglycerides. The present inventors have now produced, using the mutants disclosed in EP0341796, certain unsaturated dioic acids, some of which are novel per se, which have been found to have surprisingly enhanced properties for use in the treatment of skin for medical and cosmetic purposes.

SUMMARY OF THE INVENTION

In a first aspect the invention provides a poly-unsaturated dioic acid (i.e. a dioic acid comprising 2 or more carbon/carbon double bonds) having between 8 and 16 carbon atoms (inclusive), excluding those compounds in the group consisting of: 2,5 octadienedioic acid; 1,7 octadienedioic acid; 2,4,6 octatrienedioic acid; 1,3,5,7 nonatetraene dioic acid 2,5,8 decatrienedioic acid; 3,6 dodecadienedioic acid; and 3,13 hexadecadienedioic acid.

The compounds specifically excluded above are known from various prior art publications (e.g. Grundman, 1937 Ber. 70B, 1148–1153).

The novel compounds claimed are all capable of being synthesised by means of a novel method, detailed further below.

It is preferred that the compound is a dioic acid with an even-length hydrocarbon chain. Particularly preferred are the $C_{16}$ compounds.

Another preferred feature is that the carbon/carbon double bonds are separated by two carbon/carbon single bonds (i.e. double bonds may preferably be situated at carbon atoms 3 and 6, or 2 and 5 etc.), as such compounds are those most readily produced by the novel method.

Surprisingly, it has been found by the present inventors that the novel unsaturated dioic acids, and indeed unsaturated dioic acids in general (especially $C_{16}$ and $C_{18}$ unsaturated dioic acids) possess much greater activity than their saturated dioic acid counterparts, as anti-microbial agents and as cosmetic agents.

The prior art teaches that conditions susceptible to treatment with dioic acids include: acne (U.S. Pat. No. 4,386,104); wrinkles (EP 336880); malignant melanoma (U.S. Pat. No. 4,818,768); dermatoses (EP 229654); hyperpigmentary dermatosis and eczema (U.S. Pat. No. 4,292,326); rosacea (EP 890308); lentigo (JP 91024412) and seborrhoea (DE 3133425) and impetigo.

Similarily, the prior art teaches that some dioic acid derivatives are also effective in the treatment of certain conditions. Such compounds include esters and salts (U.S. Pat. No. 4,818,768) and mercapto-derivatives of dioic acids (U.S. Pat. No. 4,292,326). Other references to the utility of dioic acid derivatives may be found, for example, in JP 58170713, EP 0297436 and EP 0305407. German patent application No. DE 40 33 567 discloses, inter alia, mono ester derivatives of $C_3$–$C_{14}$ (main hydrocarbon chain) dioic acids (which may be saturated or unsaturated) as sebosuppressive agents for use in cosmetic or pharmaceutical applications for topical use on the hair and skin.

Thus in a second aspect the invention provides a method of treating human skin for medical or cosmetic purposes, comprising the use of an unsaturated dioic acid and/or a derivative of an unsaturated dioic acid, the derivative comprising 15 to 22 carbon atoms in the main hydrocarbon chain.

The term "main hydrocarbon chain", used with respect to dioic acid derivatives, is intended to refer to that part of the molecule situated between the oxygen atoms of the two carboxylic acid groups (or the derivatised remnants thereof). Thus, for example, derivatives having the formulae R—OOC—$CH_2$—COO—$R^1$ and R—OOC—$CH_2$—$CH_2$—COO—$R^1$ would be described as having $C_3$ and $C_4$ main hydrocarbon chains respectively.

The derivatives may be, for example, alcohols, substituted or unsubstituted amides, mono- or diesters (aryl or alkyl, especially lower alkyl esters) salts or mercapto derivatives.

Preferably, the unsaturated dioic acids employed in this method aspect of the invention contain 8 to 22 carbon atoms, most preferably 16 or 18 carbon atoms. The unsaturated dioic acid derivative preferably contains 16 or 18 carbon atoms in the main hydrocarbon chain.

Certain unsaturated dioic acids are found to be particularly active against *Propionibacterium acnes* (*P. acnes*) and *Staphylococcus aureus* (*Staph. aureus*). Thus, in general, the method of the invention may also be found useful in treating any condition where *P. acnes* and/or *Staph. aureus* is known, or suspected, to be involved in causation, maintenance or exacerbation of that condition.

In accordance with the invention, unsaturated dioic acids can be used in the treatment of a wide range of skin conditions, such as acne etc. as discussed above in connection with the prior art. Similarly, references to derivatives are intended to refer to derivatives such as esters and salts, as discussed in connection with the prior art.

Other conditions which may be susceptible to improvement by the use of unsaturated dioic acids or their derivatives include dandruff and the presence of body odour.

In addition it has been shown by the present inventors that unsaturated dioic acids are surprisingly effective as inhibitors of tyrosinase, and as inhibitors of melanin synthesis by cultivated melanoma cells, in tests used to screen compounds for activity as skin-lightening agents.

Therefore the invention provides, in a third aspect, a method of lightening skin, comprising the use of an unsaturated dioic acid or a derivative thereof.

In a fourth aspect, the invention provides a pharmaceutical or cosmetic composition comprising one or more unsaturated dioic acids and/or a derivative of an unsaturated dioic acid, the derivative comprising 15 or more carbon atoms in the main hydrocarbon chain.

Typically such compositions will be formulated for topical application to the skin. The unsaturated dioic acids and their derivatives are readily incorporated into such compositions which, for example, may take the form of creams, lotions or gels. Suitable formulations are very well known to those skilled in the art and are disclosed, for example, in U.S. Pat. No. 4,818,768.

Another aspect of the invention thus provides a method of making an anti-microbial or skin-lightening composition for topical application to the skin, comprising mixing an effective amount of an unsaturated dioic acid or a derivative thereof with a dermatologically acceptable cosmetic or pharmaceutical carrier.

The invention further provides use of an unsaturated dioic acid, and/or a derivative of an unsaturated dioic acid, the derivative comprising 15 or more carbon atoms in the main hydrocarbon chain, as an active therapeutic substance.

The invention also provides for use of an unsaturated dioic acid, or a derivative thereof, as a skin-lightening and/or anti-microbial agent.

The dioic acids used in such compositions may be prepared by the novel method disclosed below. Alternatively they may be prepared using known methods, for example as disclosed in EP 0 296 506, or as taught by Uemura et al. (1988, Proceedings of World Conference on Biotechnology for the Fats and Oil Industry, American Oil Chemists Society); Buhler & Schindler (1984, in "Aliphatic Hydrocarbons in Biotechnology", Rehm & Reed (Eds.) 169, Verlag Chemie, Weinheim) or by Picataggio et al. (1992, Biotechnology 10, 894–898).

Certain unsaturated dioic acids may conveniently be produced from longer chain unsaturated substrates using the mutants disclosed in EP 0341796, which previously have been used to make saturated compounds. Therefore, in a further aspect, the invention provides a method of preparing unsaturated dioic acids by limited beta oxidation (chain shortening) of longer chain unsaturated substrates using a yeast propagated in a growth medium.

Preferably the unsaturated dioic acids produced are $C_8$–$C_{22}$, most preferably $C_{16}$ or $C_{18}$.

Yeasts suitable for the purpose are disclosed in EP 0341796 and in Casey et al., ((1990) Journal of General Microbiology 136, 1197–1202). Such strains (eg *Candida cloacae* 5GLA12, abbreviated to "LA12") exhibit limited or reduced beta-oxidation activity.

Conveniently the yeasts are supplied with esterified unsaturated fatty acids, preferably as triglyceride esters such as oil. Particularly suitable examples include unsaturated oils such as sunflower oil and olive oil.

Preferably, the oils used as starting materials are triglycerides in which the predominant unsaturated long chain fatty acid is a $C_{16-22}$, or more preferably, a $C_{20}$ or $C_{18}$ compound. Preferably the substrate material is predominantly polyunsaturated. Fermentation by yeast strains such as LA12 can result in the production of mixtures of chain-shortened, unsaturated dioic acids (typically $C_8$–$C_{18}$ compounds). These mixed products can be separated into fractions, for example by differential solvent extraction.

If one assumes that there is random removal of $C_2$ units during beta-oxidation, and that no isomerisation of the products occurs, the following products may be predicted to be formed when using oleic acid as a substrate:
cis-7-hexadecene dioic acid; cis-5-tetradecene dioic acid; cis-7-tetradecene dioic acid; cis-3-dodecene dioic acid; cis-5-dodecene dioic acid; cis-3-decene dioic acid; cis-5-decene dioic acid and cis-3-octene dioic acid.

From linoleic acid, the following products may be expected:
cis-6, 9-hexadecadiene dioic acid; cis-4, 7-hexadecadiene dioic acid; cis-5, 8-tetradecadiene dioic acid; cis-4, 7-tetradecadiene dioic acid; cis-2, 5-tetradecadiene dioic acid; cis-3, 6-dodecadiene dioic acid; cis-4, 7-dodecadiene dioic acid; cis-2, 5-dodecadiene dioic acid; cis-3, 6-decadiene dioic acid; cis-2, 5-decadiene dioic acid; cis-2, 5-octadiene dioic acid; cis-4-decene dioic acid and cis-2-octene dioic acid.

Likewise, the predicted products using linolenic acid as a starting material are as follows:
cis-4, 7, 10-hexadecatriene dioic acid; cis-6, 9, 12-hexadecatriene dioic acid; cis-2, 5, 8-tetradecatriene dioic acid; cis-4, 7, 10-tetradecatriene dioic acid; cis-2, 5, 8-dodecatriene dioic acid; cis-3, 6-dodecadiene dioic acid; cis-2, 5, 8-decatriene dioic acid; cis-3, 6-decadiene dioic acid; cis-4-decene dioic acid; cis-2, 5-octadiene dioic acid; cis-4-octene dioic acid and cis-2-octene dioic acid.

In all cases, the product mixture will contain small amounts of products of the same chain length as the starting compound.

Indeed, whilst the preferred substrates are fatty acid esters (particularly $C_{18}$ fatty acid esters), the products of the fermentation depend upon the starting substrate. Thus, by varying the substrate, a whole range of unsaturated dioic acids may be prepared.

Some suitable substrates are identified in EP 0 229 252 and include $C_{10}$–$C_{24}$ alkenes and other unsaturated hydrocarbons such as unsaturated alkanols (especially $C_{16}$, $C_{18}$ and $C_{22}$ unsaturated alkanols), the corresponding monocarboxylic acids, or their hydroxycarboxylic acid derivatives.

Naturally, where trans-unsaturated compounds are the starting compounds, trans-unsaturated products will result.

It is a highly preferred feature that the yeast employed for the process is not propagated under conditions of nitrogen limitation. Instead, (unlike the method described in EP 0341796), the yeast is grown under conditions which are comparatively enriched for nitrogen, wherein alteration of pH affects the chain shortening beta-oxidation activity of the organism.

Thus, it is a found that the product profile of the fermentation process may conveniently be modified by alteration of the pH of the fermentation medium during the production of the unsaturated dioic acids. In particular, it is possible to alter the relative concentrations of the different lengths of dioic acid molecules in this way. For example, by reducing the pH from 7.5 to 7.1 during fermentation of olive oil, it is possible to increase the relative amount of the $C_{12}$ unsaturated dioic acid.

This is significant because certain fractions of the fermentation products may have especially advantageous properties for particular intended uses.

The different fractions of different products may be obtained from the culture medium by extracting with diethyl ether after adjustment of the aqueous phase to various different acidic pHs.

BRIEF DESCRIPTION OF THE DRAWINGS

The different aspects of the invention can be better understood by reference to the following illustrative examples and drawings in which.

EXAMPLE I

Figure 1:
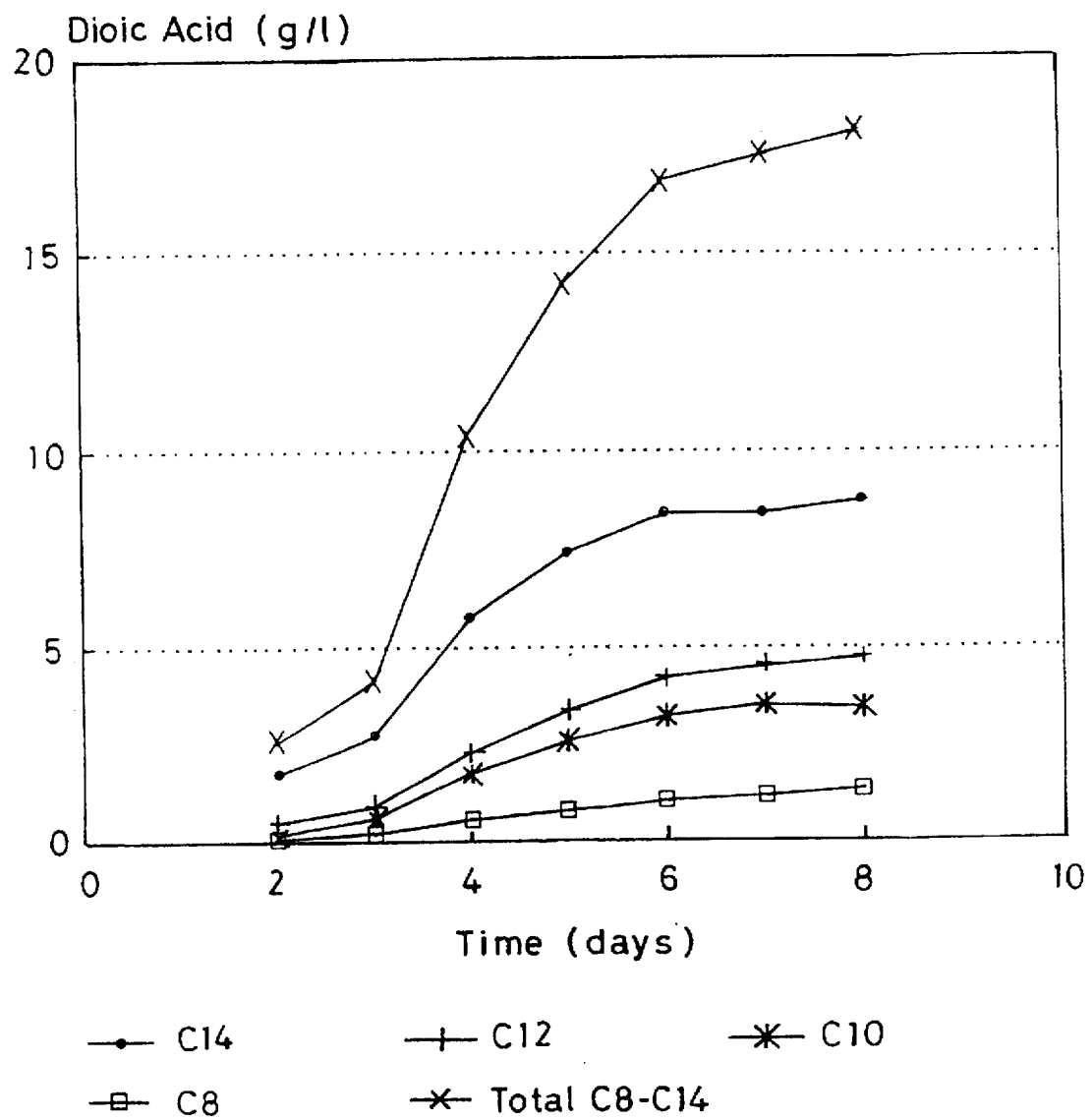
FIG. 1 is a graph of dioic acid concentration (grams per litre) against time, using sunflower oil as a substrate.

Production of Medium chain unsaturated dioic acids by fermentation

A beta-oxidation mutant of *Candida cloacae* produced by mutagensis using nitrosoguanidine (mutant LA12, see EP0341796 and see also Casey et al., J. Gen. Microbiol (1990), 136, 1197–1202) was used to produce $C_8$–$C_{14}$ unsaturated dioic acids from triglycerides such as olive oil and sunflower oil which contain high levels of unsaturated fatty acids.

A chemically defined medium was used as shown below:

| | | |
|---|---|---|
| Sucrose | 20 g/l | |
| (NH$_4$)$_2$HPO$_4$ | 6 g/l | |
| KH$_2$PO$_4$ | 6.4 g/l | autoclave 20 |
| Na$_2$SO$_4$ | 1.5 g/l | mins at 121° C. |
| Triglyceride (eq olive Oil or sunflower oil) | 10–40 ml/l | |
| ZnSO$_4$.7H$_2$O | 20 mg/l | |
| MnSO$_4$.4H$_2$O | 20 mg/l | |
| FeSO$_4$.7H$_2$O | 20 mg/l | |
| MgCl$_2$.6H$_2$O | 2 /gl | filter sterilise |
| Biotin | 100 mg/l | and add aseptically |
| Pantothenate | 6 mg/l | when fermenter cool |
| Thiamine | 8 mg/l | |
| Nicotinic acid | 30 mg/l | |
| Pyridoxine | 20 mg/l | |

The fermenter conditions were:

| | | |
|---|---|---|
| Growth pH: | 6.8 | maintained by |
| Production pH: | 7.4–7.5 | auto-addition of |
| Temperature: | 30° C. | 10N NaOH |
| Aeration: | 0.1 v/v/m air | |
| Impeller speed: | 800–1000 rpm | |
| Fermenter volume: | 2.5 L | |
| Inoculum: | 2% | |
| Fermenter type: | LSL fitted with foam breaker | |

The medium (2.5 L) was inoculated with 2% (v/v) of a 24 hr culture of *Candida cloacae* beta-oxidation mutant LA12 grown on yeast extract (5 g/l), sucrose(10 g/l), peptone (5 g/l) medium. The culture was grown for 20 hrs at pH 6.8 then 20 ml/l of oil was added and the pH increased to 7.4–7.6 to initiate production of the medium chain unsaturated dioic acids. The oil was either sunflower oil or silica-purified olive oil. During production of the dioic acids, the RQ (respiratory quotient) value fell to about 0.6. Aliquots (10–20 ml) of fermenter broth were removed daily for lipid analysis and additional oil was added as required.

The fermentation was harvested when production ceased at 8–12 days.

Medium chain unsaturated dioic acids were isolated from fermenter broths by acidification to pH 6 with HCl then extraction with diethyl ether to isolate a $C_{12}$–$C_{14}$ rich fraction. The broth was then further acidified with HCl to ca. pH2.0 and further extracted with diethyl ether to isolate a $C_8$–$C_{10}$ rich fraction. For isolation of the mixed acids the broth pH was decreased from 7.5 to ca. 2.0 in one step then extracted with diethyl ether.

Solvent was removed from the dioic acid fractions by rotary evaporation.

Figure 2:
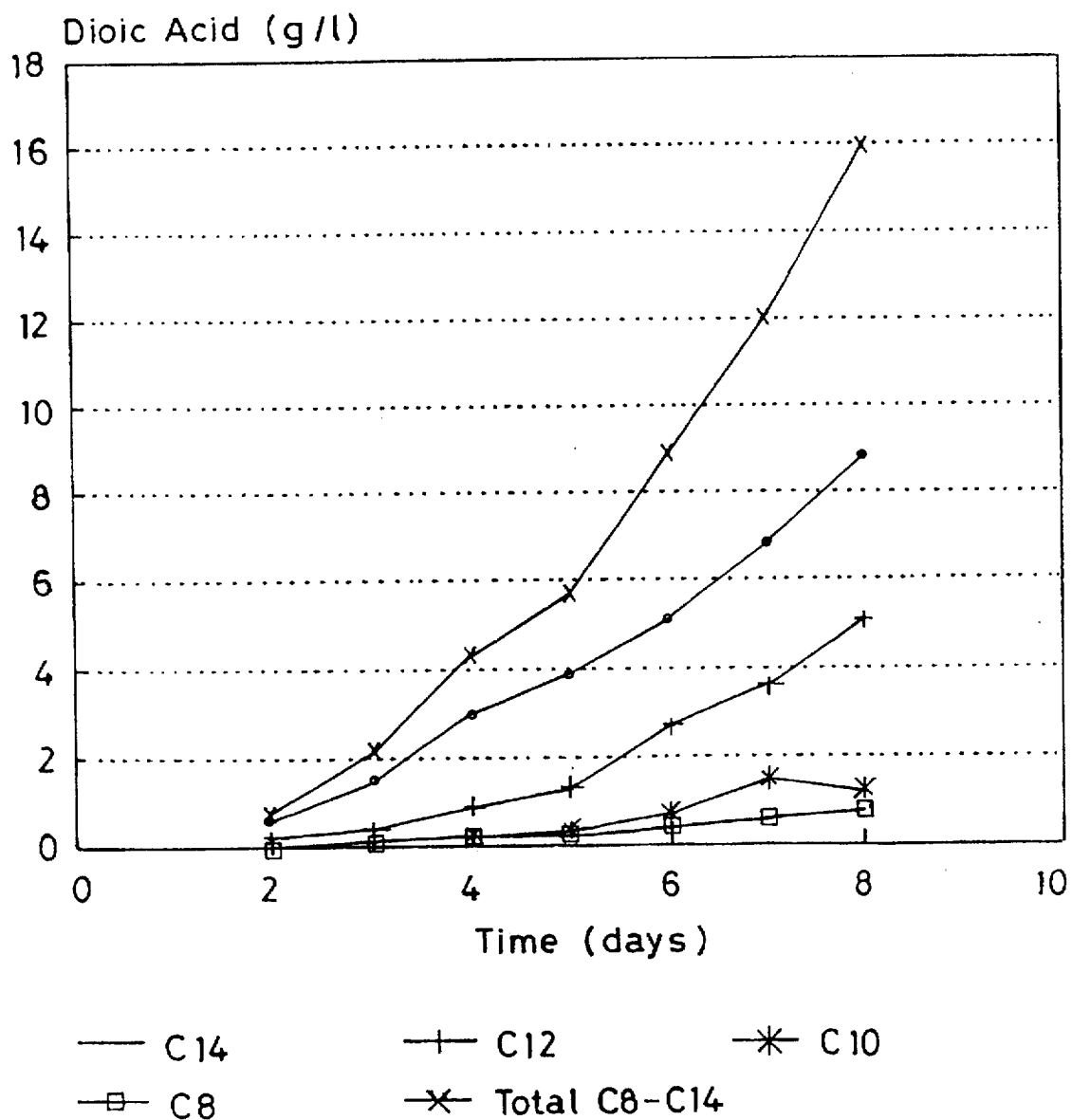
FIG. 2 is a graph of dioic acid concentration (grams per litre) against time, using olive oil as a substrate.

A time course of medium chain unsaturated dioic acid production from sunflower oil (SFO) and silica-purified olive oil (OO) is shown in FIGS. 1 and 2 respectively.

FIG. 1 shows the production of $C_8$–$C_{14}$ unsaturated dioic acids individually and in total, using sunflower oil as the substrate. The rate of production of unsaturated medium chain dioic acids increased rapidly between days 3 and 4 but declined virtually to zero by day 8, such that by that time the concentration of dioic acids was more or less constant.

FIG. 2 shows the production of $C_8$–$C_{14}$ unsaturated dioic acids individually and in total, using olive oil as the substrate. In this instance, the rate of production of dioic acids showed a less sudden increase but was continuing to rise at day 8.

In both cases, the larger dioic acids ($C_{14}$, $C_{12}$) constituted a greater percentage of the total than did the shorter chain dioic acids ($C_{10}$, $C_8$), although the precise product profile did vary between the two substrates (eg relatively more $C_{10}$ product was obtained using sunflower oil as the substrate).

These data are also represented in tabular form in Table 1.

EXAMPLE II

Use of pH to alter product profile

At a production pH of 7.4–7.6 the dominant species from oils (eg olive oil) containing $C_{18}$ unsaturated fatty acids is the $C_{14}$ unsaturated dioic acid.

Figure 3:
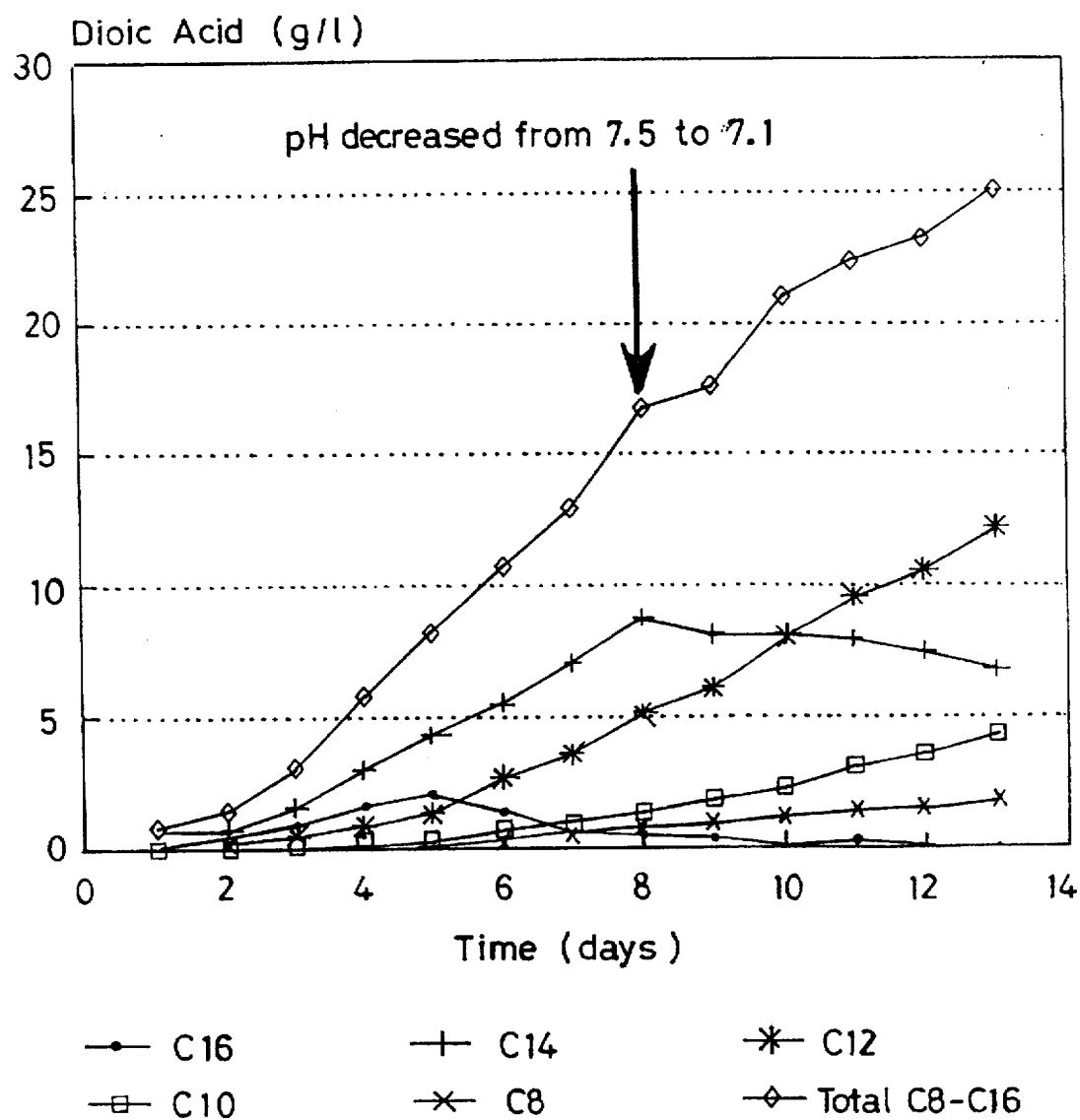
FIG. 3 is a graph of dioic acid concentration (grams per litre) against time, using olive oil as a substrate with altered pH conditions.

However, if the production pH is decreased from 7.4–7.6 to around 7.1, the $C_{12}$ unsaturated dioic acid becomes the dominant species. Fermentation was performed as detailed in the above examples until fermentation day 8 when the pH was dropped to 7.1 resulting in 'turn-over' of the $C_{14}$ species and an increase in $C_{12}$ production. The results are illustrated in FIG. 3.

TABLE 1

| | g/l Dioic Acid | | | | | | | | | |
|---|---|---|---|---|---|---|---|---|---|---|
| Fermentation | C14 | | C12 | | C10 | | C8 | | TOTAL C8–C14 | |
| Time (Days) | SFO | OO | SFO | OO | SFO | OO | SFO | OO | SFO | OO |
| 2 | 1.7 | 0.6 | 0.5 | 0.2 | 0.2 | — | 0.1 | — | 2.5 | 0.8 |
| 3 | 2.7 | 1.5 | 0.9 | 0.4 | 0.6 | 0.1 | 0.2 | 0.1 | 4.1 | 2.1 |
| 4 | 5.7 | 3.0 | 2.3 | 0.9 | 1.8 | 0.2 | 0.6 | 0.2 | 10.4 | 4.3 |
| 5 | 7.4 | 3.9 | 3.4 | 1.3 | 2.6 | 0.3 | 0.8 | 0.2 | 14.2 | 5.7 |

TABLE 1-continued

| | g/l Dioic Acid | | | | | | | | | |
|---|---|---|---|---|---|---|---|---|---|---|
| | C14 | | C12 | | C10 | | C8 | | TOTAL C8–C14 | |
| Fermentation Time (Days) | SFO | OO | SFO | OO | SFO | OO | SFO | OO | SFO | OO |
| 6 | 8.4 | 5.1 | 4.2 | 3.7 | 3.2 | 0.7 | 1.0 | 0.4 | 16.8 | 8.9 |
| 7 | 8.4 | 6.8 | 4.5 | 3.6 | 3.5 | 1.0 | 1.1 | 0.6 | 17.5 | 12 |
| 8 | 8.7 | 8.8 | 4.7 | 5.1 | 3.4 | 1.2 | 1.3 | 0.8 | 18.1 | 15.9 |

FIG. 3 shows the production of $C_8$–$C_{16}$ unsaturated dioic acids individually and in total, using olive oil as the substrate where the pH is adjusted on day 8 from 7.5 to 7.1. As noted in FIG. 2, the total production of dioic acids continues to increase after day 8 when using olive oil as a substrate. However the product profile is significantly affected. Until day 8, the concentration of the $C_{14}$ dioic acid continued to increase and was the most-concentrated dioic acid product. However, after that point, in the conditions of reduced pH, the concentration started to decline, whereas the $C_{12}$ product continued to increase, such that after day 10 the $C_{12}$ dioic acid represented the major product.

These data are also shown in tabular form in Table II.

This experiment shows that the product profile can be controlled to some extent by the production pH. The rate of $C_8$–$C_{16}$ dioic production remains substantially linear after alteration of the production pH.

EXAMPLE III

Tyrosinase Inhibition Assay

Inhibition of tyrosinase activity is used to identify potential skin whitening agents. Assays of tyrosinase inhibition were performed according to the methods of Humada and Mishima (Br. J. Derm. (1972) 86, 385–394).

All solutions were freshly prepared using 0.1M sodium phosphate buffer (pH 6.8) as diluent. These were:
40 mM Inhibitor stock solution: from which serial dilutions were made to obtain the following concentrations of 4.0, 0.4 and 0.04 mM inhibitor,

TABLE II

| Fermentation Day | Dioic Acid (g/l) | | | | | Total |
|---|---|---|---|---|---|---|
| | $C_{16}$ | $C_{14}$ | $C_{12}$ | $C_{10}$ | $C_8$ | $C_8$–$C_{16}$ |
| 1 | 0.1 | 0.6 | 0.1 | 0 | 0 | 0.8 |
| 2 | 0.52 | 0.7 | 0.2 | 0 | 0 | 1.42 |
| 3 | 0.9 | 1.5 | 0.4 | 0.1 | 0.1 | 3.0 |
| 4 | 1.6 | 3.0 | 0.9 | 0.2 | 0.1 | 5.8 |
| 5 | 2.1 | 4.4 | 1.3 | 0.3 | 0.2 | 8.3 |
| 6 | 1.5 | 5.5 | 2.7 | 0.7 | 0.4 | 10.8 |
| 7 | 0.6 | 7.1 | 3.6 | 1.0 | 0.6 | 12.9 |
| 8 | 0.6 | 8.8 | 5.1 | 1.4 | 0.8 | 16.7 |
| Change of pH from 7.5–7.1 | | | | | | |
| 9 | 0.4 | 8.2 | 6.1 | 1.9 | 0.9 | 17.5 |
| 10 | 0.13 | 8.2 | 8.0 | 2.3 | 1.2 | 21.0 |
| 11 | 0.25 | 8.0 | 9.6 | 3.1 | 1.4 | 22.35 |
| 12 | 0.1 | 7.5 | 10.6 | 3.6 | 1.5 | 23.2 |
| 13 | 0.1 | 6.8 | 12.2 | 4.3 | 1.8 | 25.2 |

Salt solution: containing copper sulphate (100 uM) and magnesium chloride (100 mM), Enzyme solution: 1 ml mushroom tyrosinase (2000–4000 units per mg), and Substrate solution: 48 mg dihydroxyphenylalanine (DOPA)/100 ml.

The enzyme and DOPA solutions were prepared immediately before use as they are light sensitive.

The inhibition of tyrosinase-catalysed oxidation of DOPA by dicarboxylic acids was followed spectrophotometrically by monitoring dopachrome formation at a wavelength of 492 nm. The reaction was performed in 96-well microtitre plates with the addition of 30 ul inhibitor (or buffer for the control), 50 ul buffer and 20 ul salt solution. DOPA (50 ul) was added to start the reaction and each plate shaken for 30 seconds. Absorbance readings were taken after 10 minutes using a microtitre plate reader (Titertek Multiscan).

Results of the tyrosinase inhibition assay showed that, like azelaic acid, the unsaturated medium chain dioic acids were found to be effective tyrosinase inhibitors resulting in at least 50% inhibition of enzyme activity when present at 10 mM concentration. This is surprising because azelaic acid is a saturated dioic acid and therefore has markedly different properties. Thus azelaic acid is a crystalline solid at room temperature whilst $C_8$/$C_{10}$ unsaturated dioic acids are low melting-point oily substances.

It is possible that the enzyme thioredoxin reductase is a more significant enzyme than tyrosinase with respect to dioic acid-mediated inhibition of skin pigmentation. Recent research (described by Fitton & Goa in Drugs 41 (5), 780–798 (1991) has shown that azelaic acid inhibits thioredoxin reductase. In the light of the disclosure in this specification the skilled worker would therefore expect unsaturated dioic acids to be inhibitors of this enzyme as well.

EXAMPLE IV

Inhibition of Melanin Production

In a further assay to complement Example III, the effects of unsaturated dioic acids on in vitro melanocyte cultures were investigated.

Pigment producing cells derived from a mammalian melanoma were grown in culture by standard methods. Preferred cell lines are B16 (disclosed in EP 0 338 104) or S-91 (e.g. ATCC CCL 51.3, clone M-3) cells, but other lines or primary mouse or human melanocytes can be used.

Melanoma cells were grown in a complete cell culture medium (such as that described in EP 0 308 919) to approximately ⅓ confluence. The composition to be tested was then added to the culture medium.

The cells were cultured for a further period of 4 days and the amount of melanin produced was assayed by measuring the absorbance at 540 nm of the total melanin extracted from the culture medium and from the harvested cells.

Figure 4:
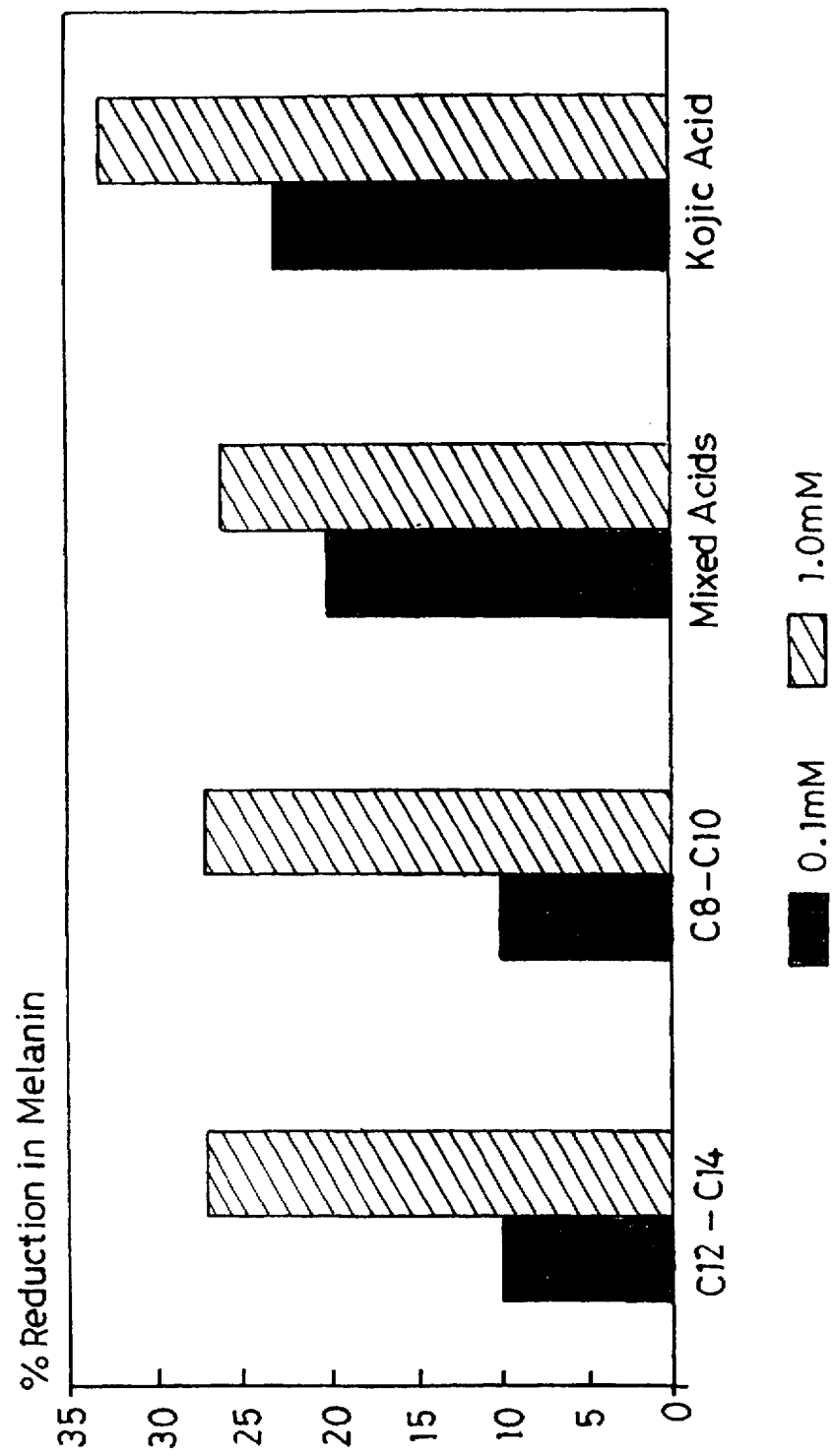
FIG. 4 is a bar chart showing percentage melanin reduction for medium chain dioic acids obtained from sunflower oil.

The method described above was used to assess the ability of compositions comprising unsaturated dioic acids ($C_{12}$–$C_{14}$ fraction, $C_{8-10}$ fraction, or mixed acids), at 0.1 mM or 1.0 mM, to reduce the amount of melanin produced by melanocyte cultures, relative to a negative control culture. Kojic acid (a substance used as a skin lightening agent) was used as a positive control. The results are shown in FIG. 4, which is a bar chart showing the percentage reduction in melanin in the treated cultures compared to the untreated control.

It was found that the various dioic acid fractions had substantially similar properties in this respect.

EXAMPLE V

Determination of antimicrobial activity

The Minimum Inhibitory Concentration (MIC) of each of various unsaturated dicarboxylic acid mixtures was determined in the presence and absence of 10% Intralipid (Kabi Pharmacia, Inc.) using the agar dilution technique for susceptibility of 32 strains of *Propionibacterium acnes* and of 32 strains of various genera of aerobic bacteria. The method was as set out below.

A 5% stock solution for each agent was prepared by adding 10 grams of the dioic acid material to 200 milliliters of double strength Tryptic Soy Broth (TSB), (Baltimore Biological Laboratories). The pH of each solution was adjusted to 7.0±0.2 with sodium hydroxide.

For each organic acid two sets of 200 ml capacity bottle/flasks were numbered 1 to 9. To each bottle was added 50 cc of double strength TSB. From the 5% stock solution, 50 cc of TSB were transferred to bottles #1 and #2. Serial transfers of 50 cc are made from bottle #2 through to bottle #8. Bottle #9 of each set contained only 50 cc of double strength TSB, without any dicarboxylic acid. To all 18 bottles were added 2 grams of granulated agar (BBL).

All bottles were autoclaved at 121° C., 15 psi for 15 minutes and then held at 50° C. in a water bath.

To one set of bottles #1–9 were added 50 cc of hot, sterile water. The bottles were swirled to mix the contents and 25 cc was poured into each of four petri dishes and allowed to solidify. To the second set of bottles were added 50 cc of Intralipid (pre-warmed to 50° C). The contents were then mixed and poured as above. Standard inocula of the test organisms were prepared by matching the bacterial suspension in 0.85% PSS (physiological saline solution) to a 0.5 McFarland Standard and diluting ten-fold to yield 107 CFU (colony forming units). The inocula were loaded into 32 wells of a steers replicator. The multi-prong inoculator delivers 0.001 to 0.002 cc resulting in a final inoculum of 104 CFU per spot.

Plates were inoculated from the lowest to highest concentration (to reduce the effects of "carry-over" of the inoculum), and allowed to dry. The plates were then inverted and incubated at 35° C. for 24 hours. Plates inoculated with *Propionibacterium acnes* strains were incubated under anaerobic conditions for seven days at 35° C.

The agent-free control plates (#9) were examined at the end of the incubation for viability and signs of contamination. End-point MIC values were determined by observing the plate of lowest concentration of agent that inhibited visible micro-organism growth.

The results are summarised in Table III, which shows the MIC for medium chain unsaturated dioic acids ("Mixed dioic Acids", i.e. $C_8$–$C_{14}$ mixed dioic acids), a $C_{12}$ enriched fraction, and for the $C_{18:1}$ mono-unsaturated compound, compared with Azelaic acid, for a range of micro-organisms. The data represent the results of experiments which were generally conducted on several different strains of each species (e.g. *P. acnes* strains ATCC 6919 and 29399 [ATCC stands for American Type Culture Collection]; *Staph. aureus* strains ATCC 25923, 35556 and 29213; *Staph. epidermidis* ATCC 35984, 31432 and 14490; *Micrococcus sedentarius* ATCC 27574; *M. luteus* ATCC 27141, 9341, and 15957; *Brevibacterium epidermidis* ATCC 35514; *Corynebacterium minutissium* ATCC 23347, 23348 and 23349). The presence or absence of "Intralipid" had no significant effect. A slight difference was observed only for the $C_{18:1}$ mono-unsaturated compound, where there was a suggestion that intralipid increased the MIC for taph. aureus and decreased the MIC for *P. acnes* and *M. luteus*.

TABLE 3

MIC AGAR DIFFUSION TEST FOR AZELAIC Vs UNSATURATED DIOIC ACIDS

| | | DICARBOXYLIC ACID TYPE (MIC %) | | | | | |
|---|---|---|---|---|---|---|---|
| Strain | Source | Azelaic acid | Mixed dioic acids ex Olive oil | $C_{12}$ enriched mono unsat dioic acids ex Olive oil | Mixed dioic acids ex Sunflower oil | $C_{18:1}$ dioic acid ex Oleic acid | $C_{18:1}$ dioic acid ex Oleic acid + "Intralipid" |
| *Propionibacterium acnes* | ATCC 6919 | 1.25 | 0.31 | 0.31 | 0.31 | 0.04 | 0.02 |
| *Propionibacterium acnes* | ATCC 29399 | 1.25 | 0.31 | 0.31 | 0.62 | 0.04 | 0.02 |
| *Staphylococcus aureus* | ATCC 25923 | 2.5 | 0.62 | 1.25 | 1.25 | 0.07 | 0.15 |
| *Staphylococcus aureus* | ATCC 35556 | 2.5 | 0.31 | 0.31 | 0.62 | 0.07 | 0.31 |
| *Staphylococcus aureus* | ATCC 29213 | 2.5 | 1.25 | 0.62 | 2.5 | 0.15 | 0.31 |
| *Staphylococcus epidermidis* | ATCC 35894 | >2.5 | 1.25 | 0.62 | 2.5 | 0.31 | 0.31 |
| *Staphylococcus epidermidis* | ATCC 31432 | >2.5 | 1.25 | 0.62 | 2.5 | 0.31 | 0.31 |
| *Staphylococcus epidermidis* | ATCC 14490 | >2.5 | 1.25 | 0.62 | 2.5 | 0.31 | 0.31 |
| *Micrococcus sedentarius* | ATCC 27574 | 2.5 | 0.15 | 0.62 | 0.62 | 0.15 | 0.07 |
| *Micrococcus luteus* | ATCC 27141 | 2.5 | 0.15 | 0.62 | 0.62 | 0.15 | 0.07 |
| *Micrococcus luteus* | ATCC 9341 | >2.5 | 1.25 | 0.62 | 0.62 | 0.15 | 0.07 |
| *Micrococcus luteus* | ATCC 15957 | >2.5 | 1.25 | 0.62 | 0.62 | 0.15 | 0.07 |
| *Brevibacterium epidermidis* | ATCC 35514 | >2.5 | 0.62 | 0.62 | 0.62 | 0.15 | 0.15 |
| *Brevibacterium epidermidis* | NCDO 2285 | >2.5 | 0.62 | 0.62 | 0.62 | 0.15 | 0.15 |
| *Corynebacterium minutissium* | ATCC 23347 | >2.5 | 0.62 | 0.62 | 0.62 | 0.15 | 0.15 |
| *Corynebacterium minutissium* | ATCC 23348 | >2.5 | 0.62 | 0.62 | 0.62 | 0.15 | 0.15 |
| *Corynebacterium minutissium* | ATCC 23349 | >2.5 | 0.62 | 0.62 | 0.62 | 0.15 | 0.15 |
| *Pseudomonas aeruginosa* | ATCC 27853 | >2.5 | >2.5 | >2.5 | >2.5 | >2.5 | >2.5 |
| *Escherichia coli* | ATCC 25922 | 2.5 | >2.5 | >2.5 | >2.5 | >2.5 | >2.5 |
| *Candida albicans* | ATCC 18804 | >2.5 | >2.5 | >2.5 | >2.5 | >2.5 | >2.5 |

*P. acnes* is the main causative agent of acne, thus efficacy against this organism indicates a usefulness in the prevention and treatment of acne. *Staphylococcus aureus* is a pathogenic Gram positive organism commonly associated with boils and abscesses. *Candida albicans* is a resistant yeast included as a negative control. *Pseudomonas aeruginosa* and *Escherichia coli* are both common Gram negative organisms.

Unexpectedly, in all cases the unsaturated dioic acids (both medium chain and C18 compounds) were more active than azelaic acid. The compounds were particularly effective against *P. acnes*, *Staph. aureus*, and *Staph. epidermidis*. In particular the $C_{18}$ compound exhibited anti-microbial activity many times greater than that for azelaic acid.

A similar experiment was performed, using the same method, to compare the degree of inhibitory activity (for *P. acnes*) of azelaic acid, the $C_{18:1}$ dioic acid (obtained from a substrate comprising oleic acid), a mixture of $C_{18:1}$ fatty (mono-carboxylic) acid, the corresponding $C_{18:1}$ and $C_{18:2}$ dioic acids (obtained from a substrate comprising Linoleic acid), and the $C_{16:1}$ dioic acid (obtained from a substrate comprising palmitoleic acid). The results are shown below in Table IV. The MICs for azelaic acid and the $C_{18:1}$ dioic acid were essentially as before, confirming the previous results. The corresponding fatty acid had very little activity. Thus, the $C_{18:1}$ dioic acid then has almost 100× the activity of azelaic acid, although the equivalent fatty acid (oleic acid) is less active than azelaic acid.

In experiment 4, the degree of inhibition of the azelaic acid control, and therefore of the test samples also, was slightly less than that observed in previous experiments.

TABLE 4

MIC's FOR LONG CHAIN DIOIC ACIDS AGAINST *P. ACNES* ATCC 25746 Vs AZELAIC ACID AND OLEIC ACID CONTROL

| | MIC (%) | | | |
|---|---|---|---|---|
| Test material | Expt. 1 | Expt. 2 | Expt. 3 | Expt. 4 |
| Azelaic acid (control) | 5 | 5 | 5 | >5 |
| $C_{18:1}$ Fatty acid (control) | nd | nd | >5 | nd |
| $C_{18:1}$ dioic acid ex Oleic acid | 0.04 | 0.04 | 0.04 | 0.08 |
| $C_{18:2/18:1}$ dioic acid ex 60% Linoleic acid | nd | nd | nd | 0.08 |
| $C_{16:1}$ dioic acid ex Palmitoleic acid | nd | nd | nd | 0.16 |

In experiment 4 the degree of inhibition of the azelaic acid control, and therefore of the test samples also, was slightly less than previously observed. The most probable reason for this was the increased incubation period of 18 days as against 7 days for the earlier work.

The most probable reason for this was the increased incubation period of 18 days, as against 7 days for the earlier work.

We claim:

1. A pharmaceutical composition in the form of a cream, lotion or gel suitable for topical application comprising, as the active component, a compound selected from the group consisting of a mono-, di- or tri-unsaturated $C_8$–$C_{22}$ dioic acid and a pharmaceutically acceptable derivative of said unsaturated dioic acid, the derivative having 15 to 22 carbon atoms in the main hydrocarbon chain and being an alcohol, amide, ester, salt or mercapto derivative.

2. The composition according to claim 1, wherein the active component is selected from the group consisting of an unsaturated $C_{16}$ or $C_{18}$ dioic acid and said pharmaceutically acceptable derivative thereof.

3. The composition according to claim 1, wherein the composition comprises from 0.001% to 20% by weight of said active ingredient.

4. The composition according to claim 3, wherein the composition comprises from 0.01% to 1% by weight of said active ingredient.

5. A method of treating acne comprising administering to a patient in need of said treatment, an effective amount of the composition of claim 1.

6. A method of treating human skin which comprises administering to a patient an effective amount of a composition according to claim 1 for the purpose of treating a condition caused, maintained or exacerbated by *Propionibacterium acnes*.

7. A composition according to claim 1, said composition having a pH in the range of 6.8–7.2.

\* \* \* \* \*